US005372781A

United States Patent [19]
Hallett et al.

[11] Patent Number: 5,372,781
[45] Date of Patent: Dec. 13, 1994

[54] UV REACTOR ASSEMBLY WITH IMPROVED LAMP COOLING MEANS

[75] Inventors: Ronald C. Hallett, Pickering; Stephen R. Cater, Willowdale; Keith G. Bircher, Richmond Hill; J. Adele Buckley, Willowdale; R. D. Samuel Stevens, Richmond Hill, all of Canada

[73] Assignee: Solarchem Enterprises Inc., Ontario, Canada

[21] Appl. No.: 836,617

[22] Filed: Feb. 18, 1992

[51] Int. Cl.$^5$ .......................... B01J 19/12; C02F 1/32
[52] U.S. Cl. ................................ 422/186.3; 422/186; 422/24
[58] Field of Search .................... 422/186.3, 186, 24

[56] References Cited

U.S. PATENT DOCUMENTS

| | | | |
|---|---|---|---|
| 3,182,193 | 5/1965 | Ellner et al. | 250/43.5 |
| 3,462,597 | 8/1969 | Young | 250/43 |
| 3,562,520 | 2/1971 | Rippen | 250/43 |
| 3,904,363 | 9/1975 | Free | 21/102 R |
| 4,002,918 | 1/1977 | Graentzel | 250/431 |
| 4,045,316 | 8/1977 | Legan | 204/158 R |
| 4,141,830 | 2/1979 | Last | 210/637 |
| 4,179,616 | 12/1979 | Coviello et al. | 250/527 |
| 4,189,363 | 2/1980 | Beitzel | 204/157.1 R |
| 4,694,179 | 9/1987 | Lew et al. | 250/431 |
| 4,897,246 | 1/1990 | Peterson | 422/186.3 |
| 4,952,376 | 8/1990 | Peterson | 422/186.3 |
| 4,963,750 | 10/1990 | Wilson | 250/436 |
| 5,133,945 | 7/1992 | Hallett | 422/186.3 |
| 5,178,758 | 1/1993 | Hwang | 210/256 |
| 5,227,140 | 7/1993 | Hager et al. | 422/186.3 |
| 5,266,215 | 11/1993 | Engelhard | 210/748 |
| 5,266,280 | 11/1993 | Hallett | 422/186.3 |

FOREIGN PATENT DOCUMENTS

| | | |
|---|---|---|
| 3879 | 9/1979 | European Pat. Off. . |
| 3710250 | 10/1988 | Germany . |
| WO88/04281 | 6/1988 | WIPO . |
| WO92/22502 | 12/1992 | WIPO . |

Primary Examiner—Donald P. Walsh
Assistant Examiner—Daniel Jenkins
Attorney, Agent, or Firm—Lowe, Price, LeBlanc & Becker

[57] ABSTRACT

A reactor assembly is provided for destroying contaminants in fluids by the application of UV radiation to promote the destruction of the contaminants. The reactor assembly has a vertically orientated reactor chamber with a centrally located lamp emitting UV radiation and operating at temperatures in excess of 700° C. A protective sheath transparent to the UV radiation encloses the lamp and isolates the lamp from reactor interior to define thereby an annular reactor space through which fluids to be treated flow. The fluids flowing through the annular reactor space and along the sheath effect a cooling of the sheath due to lamp heating. The lamp has a terminal portion at each end thereof. Each terminal portion has a temperature sensitive component. The lamp is of a sufficient length to extend the terminals beyond the end portions of the reactor which has a length equal to or greater than the arc length of the lamp. Cooling air is directed on to each of the upper and lower terminals of the lamp to cool the temperature sensitive portions thereby preventing deterioration of each lamp end due to excessive heating. In directing cooling air onto the lower terminal a pressure is developed which is greater than the pressure at the upper end of the sheath so that a control constant flow of cooling air is assured upwardly of the sheath and over the lamp. This constant flow of cooling air is assured upwardly over the sheath and over the lamp. This constant flow of cooling air is controlled to permit the lamp to operate at optimum operating temperatures to provide the necessary output of UV radiation to promote the destruction of the contaminants in the fluids.

29 Claims, 7 Drawing Sheets

UV REACTOR ASSEMBLY WITH IMPROVED LAMP COOLING MEANS

FIELD OF THE INVENTION

This invention relates to a reactor having ultraviolet (UV) lamps. The radiation from which treats a fluid medium, for example, water, air or solvent. More particularly, the reactor system is adapted to treat contaminants in the fluids by use of UV emitting lamps which operate at high temperatures normally in excess of 700° C.

BACKGROUND OF THE INVENTION

Ultraviolet radiation is an important workhorse in the industrial community for promoting chemical reactions, initiating chemical reactions, degrading organic and non-organic molecules, inducing mutations in biological systems, acting as an antiviral and bactericidal agent and the like. Normally the source of the ultraviolet radiation is emitted from an electric discharge lamp having various types of gases which when excited by the electric discharge, emit UV radiation. These lamps are generally categorized as low or medium/high intensity lamps. They may operate at low or high pressures for the gases within the lamps. Normally the lamps are of a quartz material which is transparent to the emitted UV radiation. The lamps may operate at low or high temperatures ranging from approximately 30° C. up to 1100° C. The power input of these lamps may range from less than 40 watts to in excess of 60,000 watts for developing watts of UV radiation. The lamps may be even customized to the extent that a certain portion of the UV spectrum is omitted or enhanced rather than the entire portion of the UV spectrum.

A driving force for such variety in UV lamps is that each of the above industrial applications requires lamps having different UV intensities, different wavelength of emission, operating pressure and temperatures and power requirements.

Normally the lamps, as employed in reactor systems, particularly reactor systems which contain aqueous media, have a variety of UV transparent protective sheaths within which the lamps are placed so that the lamps do not come in contact with the material being treated by the UV radiation. This technique protects the quartz of the UV lamp and the electrical connections to the lamp electrodes. Also it can facilitate lamp replacement without having to disassemble the reactor.

Another general approach for exposing fluids to UV radiation to initiate or expedite a desired chemical reaction within the fluids is to position a plurality of UV lamps around a reaction container having a vessel wall which is transparent to the UV radiation. This permits radiation emitted by the lamps to pass through the vessel walls and be absorbed by the fluids within the reaction container so as to initiate or expedite the desired reaction. Normally, the lamps as they surround the reaction vessel are enclosed. The enclosure may have UV reflective surfaces so as to direct radiation emitted by the lamps in a direction away from the reactor to reflect such radiation back towards the reactor. With the provision of several lamps within the enclosure overheating of the enclosed lamps can become a problem. An example of this type of reactor is discussed in U.S. Pat. No. 4,002,918.

Returning to the first alternative for reactor design with the lamps positioned within the fluids to be treated, two examples of this type of water treatment system are disclosed in U.S. Pat. No. 3,462,597 and 3,562,520. An annular chamber is defined between the outer cylindrical wall of the water treatment apparatus and the inner sheath of the apparatus which protects the UV radiation emitting lamp from the fluids that are passed through the annular chamber in the fluid treatment apparatus. Both systems are designed so as to enclose the lamp ends as the lamp is positioned centrally of the apparatus and enclosed by the protective sheath. The sheath is of quartz or other UV transparent material. Special sheath cleaning mechanisms are described in these arrangements. The drawbacks of those systems are discussed in detail in applicant's co-pending U.S. application Ser. No. 07/717,781 filed Jun. 17, 1991.

The systems of these two U.S. patents are quite adequate for use as an antiviral and bactericidal agent for treating drinking water. Low temperature lamps are used in accordance with standard techniques for exposing water to radiation. The lamps are totally enclosed. As demonstrated in both U.S. patents the lamp ends are completely enclosed and sealed off within the sheath. This allows replacement of air within the annular space defined between the lamp and the protective sheath with inert gases which are not oxidized by the UV radiation. This prevents the formation of ozone which is thought to be very harmful to the components used in the UV treatment systems. Completely enclosed lamps may be acceptable for systems using lamps operating at lower temperatures within the 40° to 150° C. range.

In U.S. Pat. No. 4,897,246 and its divisional application U.S. Pat. No. 4,952,376 a UV treatment system is disclosed for decontaminating various forms of waters and waste waters. The waste waters are introduced at one end of the reactor system and by use of baffles directed in a zigzag pattern flow over lamps within the reactor chamber. The reactor chamber is rectangular with a continuous flow of liquids through the reactor chamber. The lamps used in the system are of significantly higher power than the lamps used in the aforementioned water treatment systems of U.S. Pat. Nos. 3,462,597 and 3,562,520. In accordance with standard techniques the UV radiation emitting lamps are isolated from the fluids being treated by suitable protective sheaths. Also in accordance with standard practice the ends of the lamps are sealed off so as to define a sealed annular space between the lamp and the protective sheath. In this arrangement the preferred form of lamp used is a higher pressure mercury lamp, sometimes referred to as a medium pressure lamp. These lamps have been called both medium pressure and high pressure lamps in the literature. The operating characteristics for these lamps can vary a great deal. Lamps which we will refer to as medium pressure lamps are mercury lamps with pressures of 1 to 10 atm, with bulb temperatures greater than 400° C. and input power densities of 40 to 100 watts/cm of bulb length. These lamps operate at considerably higher temperatures than the low pressure UV lamps. Medium pressure lamps operate at temperatures usually in excess of 400° C. One advantage in using the high temperatures medium pressure lamps is that they are less susceptible to changes in fluid temperature. On the other hand, with low temperature low pressure UV lamps any significant change in water temperature can appreciably affect the operating temperature of the low pressure lamp and hence, affect its overall performance.

Higher intensity lamps, such as medium pressure mercury lamps are therefore preferred in this respect as discussed in U.S. Pat. No. 4,952,376. However, in view of the lamps being sealed within the protective sheath of the reactor, difficulties can be encountered in overheating of the lamps and possible deterioration as the lamp power increases. Other than cooling of the lamps as provided by fluid flowing over the protective sheaths, the temperature sensitive lamp end portions which include the electrical terminals are not adequately cooled and can from time to time overheat resulting in lamp failure. Such overheating problem with the higher temperature medium pressure lamps has therefore discouraged their use in UV treatment systems. As a result, lamps used in the system of U.S. Pat. No. 4,952,376 operate at the lower end of the temperature scale for medium pressure lamps and hence have less output compared to lamps operating at the higher end of the temperature scale.

Many commercially available systems function with the use of low temperature low pressure mercury lamps which have low power input usually in the range of 40 to 140 watts of UV power for each individual lamp. This power input usually equates to approximately 0.4–0.8 watts/cm of lamp arc length and operating temperatures less than 100° C.

There are several other disadvantages and drawbacks to the above inventions for the treatment of contaminated fluids. Low pressure lamps have good efficiency (30%) which refers to the percent output of UV between 200 nm and 300 nm, which is the important UV region for decontaminating fluids. However, low pressure lamps have a major disadvantage since they are of such low input powers (40–120 watts typically) that a very large number of lamps are required for the treatment of fluids at high flow rates. This becomes impractical since many lamps and reactor chambers have to be built and maintained. Conventional medium pressure lamps are of low efficiencies, <20%, such that again too many lamps are required and the electrical consumption is high. There is thus a need for a lamp which operates at high power with good efficiency. There are now lamps available with high power inputs and efficiencies of around 30%. These lamps have higher input per unit length of arc than do the standard medium/-pressure lamps (100–300 watts/cm compared to <100 watts/cm). The lamps also run hot with bulb temperatures in the range of 600° C.–1000° C. These factors result in much more heat being generated at the quartz surfaces of the sleeve and lead to problems with cooling of the lamps and the surrounding materials of constructions. The present invention incorporates a design that allows for proper cooling and operation of the lamps and protection of the surrounding materials. In addition, the invention allows for a method of mixing within the reactor so that treated water is removed from nearest the lamp and replaced with water farthest from the lamp resulting in better treatment performance.

SUMMARY OF THE INVENTION

According to an aspect of the invention, a reactor assembly is provided for destroying contaminants in fluids by the application of UV radiation to promote such destruction. The reactor system is designed to accommodate the use of the high temperature medium pressure lamps and comprises:

i) a vertically oriented cylindrical reactor column with an inlet at one end to introduce fluids to the reactor and an outlet at another end to remove treated fluids from the reactor, ii) a vertically oriented UV radiation emitting lamp operating at temperatures in excess of 300° C. and is positioned centrally of the reactor column, iii) a cylindrical protective sheath transparent to UV radiation for the lamp, the sheath being concentric with said lamp and isolating said lamp from reactor interior, the reactor column in combination with the sheath defines an annular reactor space through which fluids to be treated flow from the reactor inlet through to the reactor outlet, whereby fluid flow along the sheath effects cooling of the sheath due to lamp heating, iv) an end cap for each end of the reactor, the end caps having aligned centrally located openings to receive corresponding ends of the sheath, whereby each end of the sheath opens outwardly of the end cap, v) means for operatively circumferentially sealing respective end portions of the sheath to the end cap openings to retain thereby fluids being treated in the annular reactor space, vi) the lamp having a terminal portion at each end thereof, each terminal portion having a temperature sensitive component, the lamp being of a sufficient length to extend the terminals and position the temperature sensitive portions beyond each open end of the sheath, the lamp having an arc length and the reactor having a reactor length defined by the end caps, the reactor length being equal to or greater than the arc length, vii) means for supporting each terminal at each reactor end, each of the support devices having a lamp engaging portion which transverses the open ended sheath in a manner which provides air communication with sheath interior, and viii) means for directing cooling air onto each of the upper and lower terminals to cool the temperature sensitive portions and thereby prevent deterioration of each lamp end due to excessive heating, the sheath having an internal diameter greater than an external diameter for the lamp, the means for directing cooling air onto the lower terminal being adapted to develop an air pressure value at a lower end of the sheath greater than an air pressure value at an upper end of the sheath, as a result a constant flow of cooling air is assured upwardly of the sheath and over the lamp by virtue of the sheath lower and upper ends being open outwardly of the lower and upper end caps, the constant flow of cooling air is controlled to permit the lamp to operate at optimum operating temperatures.

According to another aspect of the invention, a method is provided for decontaminating a fluid. The method involves the application of UV radiation from high temperature medium pressure lamps and comprises:

i) passing the fluid to be treated through a vertically oriented cylindrical reactor chamber with the UV lamp extending along the chamber and located centrally thereof, the lamp is isolated from the chamber by an enclosing cylindrical sheath which is transparent to the UV radiation, the sheath is larger than the lamp to provide an annular space between the lamp and sheath, the reactor chamber having a reactor length which is equal to or greater than an arc length for the lamp, ii) positioning each lamp terminal end exterior of respective ends of the sheath with temperature sensitive portions of each terminal exposed beyond the sheath ends, iii) passing cooling air over respective terminal ends of the lamp to cool the temperature sensitive portions and thereby prevent deterioration of each lamp end due to excess heating during lamp operation, and iv) developing sufficient air pressure at the lower end of the sheath which exceeds air pressure at the upper end of the sheath to ensure a constant upward flow of air along the annular space within the sheath to provide thereby additional cooling for and prevent overheating of the lamp during operation at temperatures in excess of 300° C.

Further advantages and features of the invention will be apparent to those skilled in the art from the following detailed description thereof, taken in conjunction with the accompanying drawings.

BRIEF DESCRIPTION OF THE DRAWINGS

Preferred embodiments of the invention are shown in the drawings wherein.

DETAILED DESCRIPTION OF THE PREFERRED EMBODIMENTS

The reactor assembly of this invention is particularly adapted for use with high temperature, high intensity UV lamps. As will become apparent in the following discussion of the preferred embodiments where special provisions have been made in the reactor assembly to provide for fluid treatments while using high intensity UV lamps which operate at very high temperatures. In the industry of UV lamps it is generally understood that the lamps fall into three categories of low pressure, medium pressure and high pressure lamps. The pressure refers to the build up of pressure within the lamp during operation. The pressure build up is normally due to the vaporization of mercury within the lamp. Usually exciting gases are contained in the lamp which commence the arc discharge and through the arc discharge the mercury is heated to vaporization temperature to produce a vapour in the lamp which in turn during excitation cycles emits the UV radiation of the desired intensity and wavelength. Low pressure lamps have lamp wattages of about 0.01 watts/cm$^2$ and operate at temperatures less than 100° C. As defined in the literature [L. R. Kohler "Ultraviolet Radiation" John Wiley & Sons Inc. New York 1965 and J. F. Waymouth "Electric Discharge Lamps, The MIT Press, Cambridge 1978 and R. Phillips "Sources and Applications of Ultraviolet Radiation", Academic Press, Toronto 1983] medium pressure lamps have lamp wattages around 0.1 to 1.0/cm$^2$ and normally operate at temperature around 300° to 400° C. As already discussed, the embodiments of this invention are directed towards the use of the medium to high pressure lamps which operate at temperatures normally in excess of 400° C. and usually in excess of 700° C. up to 1000° C. or even higher perhaps to 1100° C. At these extremely high operating temperatures several aspects during their operation become a problem but now that they have been solved by this invention provide very useful UV treatment assemblies.

The preferred lamp for use in the system shown in the drawings is that sold by the applicant. Such UV lamps are high intensity, medium pressure, mercury vapour lamps with about 30% of the UV radiation output below 300 nm. Most of the water decontamination processes carried out in this reactor are in accordance with processes proprietary to the applicant such as described in U.S. Pat. No. 4,956,098, 5,043,079 and 5,043,080. The greater the output below 300 nm the more effective the chemical decontamination treatment.

Figure 1:
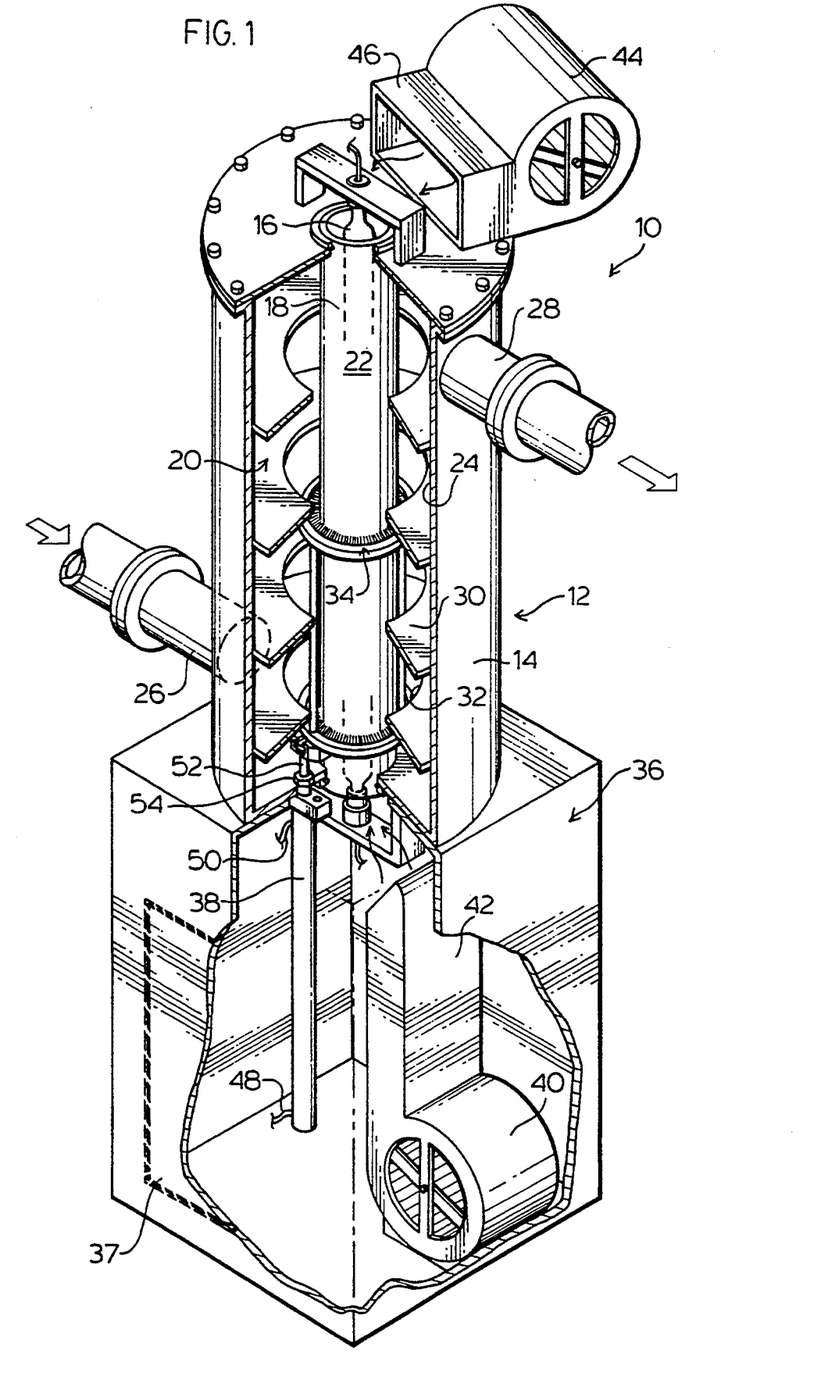
FIG. 1 is a perspective view of the reactor system according to a preferred embodiment of the invention in which a portion of the reactor outer shell is removed to permit illustration of the system for decontaminating fluids treated by the reactor.

The reactor 10 of FIG. 1 comprises a reactor vessel 12 defined by an outside reactor wall 14. According to this preferred embodiment, the reactor vessel 12 is cylindrical in shape. A high intensity medium pressure elongate lamp 16 is located centrally of and extends along the reactor vessel 12. Within the reactor vessel 12, a UV transparent protective sheath 18 is provided which encompasses and isolates the UV lamp from the interior of the reactor vessel 12. The cylindrically shaped sheath is positioned centrally of the reactor vessel thereby defining an annular space 20 between the exterior surface 22 of the protective sheath and the interior surface 24 of the reactor outside wall 14. Aqueous media to be treated within the reactor 12 flows into the annular reactor chamber 20 through an inlet conduit 26. The treated effluent flows out of the annular reactor chamber 20 through outlet 28.

According to the embodiment of FIG. 1, a plurality of baffles 30 are secured to the inside surface 24 of the outer wall 14. Each baffle is circular shaped with a central opening 32 which provides clearance for the protective sheath 18 as well as the system generally designated 34 for cleaning the protective sheath. The baffles are provided within the annular chamber 20 to ensure adequate mixing so that during the residence time for the aqueous media all portions thereof are exposed to the UV radiation from lamp 16 to provide the desired treatment for the aqueous media.

As will be discussed in more detail with respect to FIG. 2 the baffles provide an oscillating motion for the fluids in a longitudinal direction as well as a radial direction. This is quite different from the traditional arrangement of baffles in systems which normally are designed to create plug flow through the reactor. Instead, the baffle arrangement according to this invention, ensures that the liquids are well mixed as they travel through the annular reactor space as well as vary the radial distance of the fluids from the UV lamp to vary the intensity to which the fluids are exposed to the UV radiation. The highest degree of turbulence or mixing is closest to the lamp at each baffle location which renews the water at the boundary layer between the water and the quartz protection sheath. In so doing the reactor is then divided into several serially connected treatment zones or annular reactor compartments.

The reactor 12 is supported on a base 36 which houses an external drive 38 for the sheath cleaning system 34 as well as a cooling fan 40 for directing through duct 42 a flow of cooling air on to the UV lamp 16. The other end of the UV lamp is correspondingly cooled by a fan 44 directing cooling air onto the lamp tip through duct 46.

The device for reciprocating the cleaning system 34 is located externally of the reactor. A pneumatic cylinder having air pressure fed to the cylinder through lines 48 and 50 reciprocate the piston rod 52 upwardly and downwardly through the reactor annular chamber 20. The piston rod is sealed to a reactor end by gland 54 which is adequate to prevent leakage of aqueous media from within the annular reactor chamber and to prevent outside air from leaking into the fluid medium being treated. The gland and its sealing ability about the rod 52 is selected dependant upon the pressures and corrosive nature of the aqueous media to be treated. Further details of the sheath cleaning system are disclosed in applicant's copending U.S. patent application 717,781 filed Jun. 17, 1991.

Figure 2:
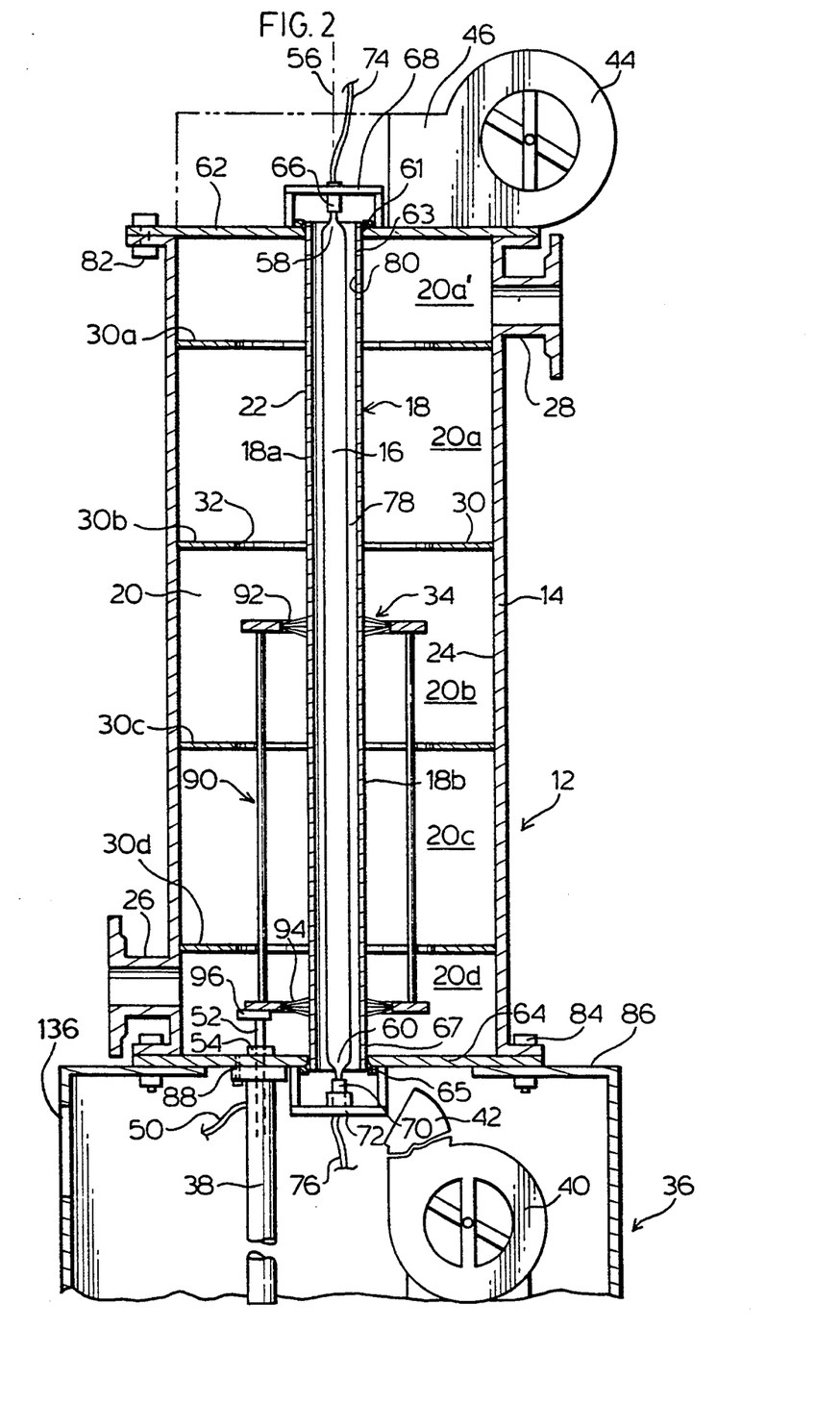
FIG. 2 is a longitudinal section through the reactor of FIG. 1.

As shown in FIG. 2, the UV lamp 16 is coincident with the longitudinal axis 56 of the cylindrical reactor 14. The lamp ends 58 and 60 extend beyond the end plates 62 and 64 for this cylindrical reactor.

The supports for the lamp ends 58 and 60 are provided externally of the end plates 62 and 64 for the reactor and are preferably formed of ceramic material. The lamp end 58 has a ceramic mount 66 which is secured in a U-shaped bracket 68. The U-shaped bracket 68 is secured to the end plate 62. Similarly, lamp end 60 has ceramic mount 70 which is secured in the U-shaped bracket 72. In turn the U-shaped bracket 72 is secured to the outside of end plate 64. The mounting brackets 68 and 72 position the lamp 16 along the longitudinal axis 56 of the reactor. Suitable electrical leads 74 and 76 are provided at each lamp end for purposes of powering the lamp. Further details of these supports shall be discussed with respect to FIGS. 6 and 7.

The quartz tube 18 is sealed at its ends to the end plate 62 and 64 to prevent leakage of aqueous media from the annular reactor chamber 20. As shown in FIG. 2, appropriate sealing rings 61 surround the end 63 of the quartz tube at end plate 62. Correspondingly, at end plate 64, sealing ring 65 surrounds and seals the end 57 to the end plate 64. Details of a preferred sealing device are shown and described with respect to the section of FIG. 7. It is appreciated that a variety of seals are available to effect the sealing of the two ends of the quartz tube to the end plate to prevent leakage. Such suitable seals include synthetic elastomers such as fluoroelastomers, which are clamped to the quartz tube end and secured to the respective end plate 62 and 64. In this manner, ready disassembly of the quartz sheath 18 from the end plates is achieved.

With the high intensity medium pressure lamps operating at temperatures in the range of 700° C. to 1000° C., external cooling is required. As already identified in FIG. 1, a cooling fan 40 directs cooling air onto the ceramic mount portion 70 of the lamp end 60. The cooling air is directed by the duct 42. Similarly on the top, near lamp end 58, a cooling fan 44 through duct 46 directs cooling air onto the ceramic mount 66. Details of the cooling system shall be discussed with respect to FIGS. 3, 4, 5 and 7 of the drawings.

The inlet 26 for the reactor is located near or adjacent the first end plate 64. Similarly, the outlet 28 is located adjacent or near the second end plate 62 for the reactor. In this manner aqueous media enters one end of the reactor, flows through the annular space 20 and over the baffles 30 for discharge through the outlet 28. The baffles 30 are clear of the apparatus 34 for removing materials deposited on the exterior surface 22 of the sheath 18. For purposes of ease of assembly, the cylindrical reactor 12 has the end plates 62 and 64 bolted thereto in the manner shown by suitable bolts 82 and 84. Bolts 84 extend through the support base upper surface 86 for purposes of securing the reactor to the base 36. The pneumatic cylinder 38 for reciprocating the cleaning device 34 is secured to end plate 64 by bolts 88. The piston rod 52 is secured to a carriage 90 for the individual brushes 92 and 94. The stroke of piston rod 52 is sufficient to ensure the brush 92 traverses the upper region 18a of the sheath and brush 94 traverses the lower region 18b of the sheath, preferably brush 94 overlaps, to at least some extent in traversing the upper region 18a.

As shown in FIG. 2 the reactor chamber 20 is divided up into a series of reactor compartments by baffles 30 which have been identified as baffles 30a, 30b, 30c and 30d. Reactor space 20d receives the incoming fluids to be treated through inlet 26. Fluids then flow upwardly of the reactor, through the reactor compartments in a sequencial manner through compartments 20c, 20b, 20a and uppermost compartment 20a'. As the liquids flow upwardly of the reactor the baffles cause the liquids to flow inwardly and outwardly relative to the protective sheath 18. This varies the radial distance of the fluids being treated relative to the lamp, hence, exposing the fluids to varying UV radiation intensities and correspondingly varying the rate of reaction for decontaminating the fluids. The baffles are designed so as to induce mixing of the liquids as they pass between the inner portion 32 of each baffle and the exterior 22 of each protective sheath. Hence, the baffles form a series of interconnected annular reactor compartments through which the fluids travel in the treatment process.

Several considerations are necessary in providing for cooling of the lamp ends as well as the lamp portion housed within the protective sheath 18. As will become apparent from a discussion of FIG. 7 the lamp ends include temperature sensitive portions which break the electrical connection with the electrodes within the lamp when the lamp ends exceed a predetermined temperature normally in excess of 350° C. It is therefore important to ensure that the lamp ends operate at a temperature below the temperature at which the electrodes break down, however, in cooling the lamp ends it is important not to overcool the lamp body as housed within the sheath 18. Overcooling of the lamp body results in decreased lamp performance and can even result in extinguishing the lamp. Extinction of lamp operation usually happens when the lamp body is cooled to the extent that vapour being formed by the electric discharge is caused to immediately condense so that the lamp never gets beyond the start-up phase or during operation is cooled to the extent that the mercury vapour condenses within the lamp. It is also important to ensure that any temperature sensitive portions of the reactor body be designed in the manner so as not to be affected by the high temperature operation of the lamp or that the portions of the reactor assembly exposed to UV radiation are of suitable materials or are protected from UV deterioration. Another factor which enters into the design considerations is protecting users from exposure to UV radiation during lamp operation. This necessitates enclosing both the lower and upper portions of the reactor so that operators cannot view directly UV radiation emitted by the lamp. It is appreciate of course that components of the reactor may be made of materials which do not reflect UV radiation so that it is only direct radiation exposure which could cause a problem with operators. As already shown with respect to FIG. 1 the bottom portion of the reactor is enclosed in a support base 36. The support base 36 normally has a door access 37 for purposes of servicing the pneumatic cylinder 38, the cooling fan 40 as well as facilitate lamp replacement. Suitable interlocks are provided such that when the door 37 is opened, the lamp is shut down to avoid exposure to UV radiation.

Figure 3:
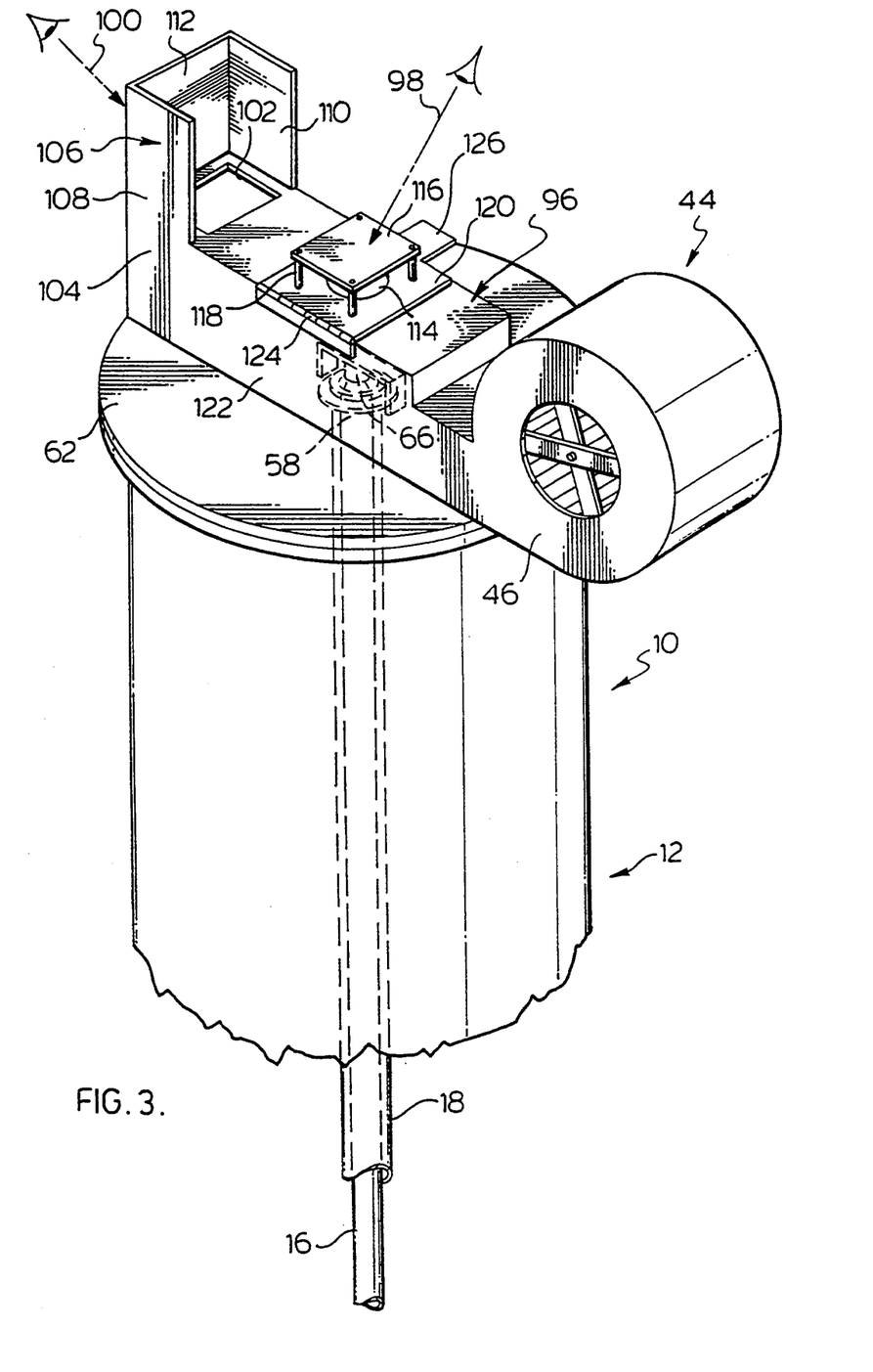
FIG. 3 is a perspective view of the top portion of the reactor of FIG. 1 as provided with an embodiment of the invention for cooling the upper end of the lamp assembly.

Similarly, the upper part of the reactor has to be enclosed by suitable enclosure connected to the outlet duct 46 of the blower or cooling fan 44. As shown in FIG. 3 an enclosure 96 is provided on the end cap 62 to prevent operators having direct eye access as indicated by arrows 98 and 100 to radiation emitted by the lamp at its upper end 58. The enclosure 96 must have openings therein to provide venting of cooling air forces into the enclosure through duct 46 by fan 44. The enclosure 96 has two openings. A first opening 102 is located at the far end 104 of the enclosure. Opening 102 is sized to allow at least some of the air generated by blower 44 to exit the enclosure through the opening 102. To prevent operators from viewing the lamp end 58 and running the risk of exposure to direct UV radiation a three sided curtain 106 is provided with opposing sides 108 and 110 and a rear side 112. The height of the rear and opposing sides is such that an operator standing on a ladder or in any other manner above the reactor cannot directly view the lamp end 58. In this way an opening is provided in the enclosure to provide for venting of air from the blower 44.

An opening 114 is also provided in the enclosure 96 directly above the lamp terminal 66. As will be discussed in more detail with respect to FIG. 5, opening 114 provides a venting of air which rises directly from within the protective sheath 18 and over the lamp terminal 66. In the event that the blower 44 shuts down before the lamp end is properly cooled the chimney effect in air rising through the sheath continues to cool the lamp end 66. The opening 114 being directly above the lamp tip 66 ensures that unrestricted upward flow of cooling air is provided.

The opening 114 has a cover plate 116 positioned over the opening 114 and supported thereabove by post 118. In this manner air can exit through the opening 114 and from beneath the plate 116. At the same time plate 116 blocks direct vision of UV radiation from lamp end 58 as indicated by arrow 98. To facilitate lamp replacement the opening 114 is provided in a hinged plate 120 which is hinged to the side 122 by piano hinge 124. A limit switch may be provided in contact with the plate 120 to sense when the plate is hinged to the open position by lifting on handle 126. Upon sensing such movement the lamp is immediately shut down to prevent operator exposure to direct UV radiation.

Figure 4:
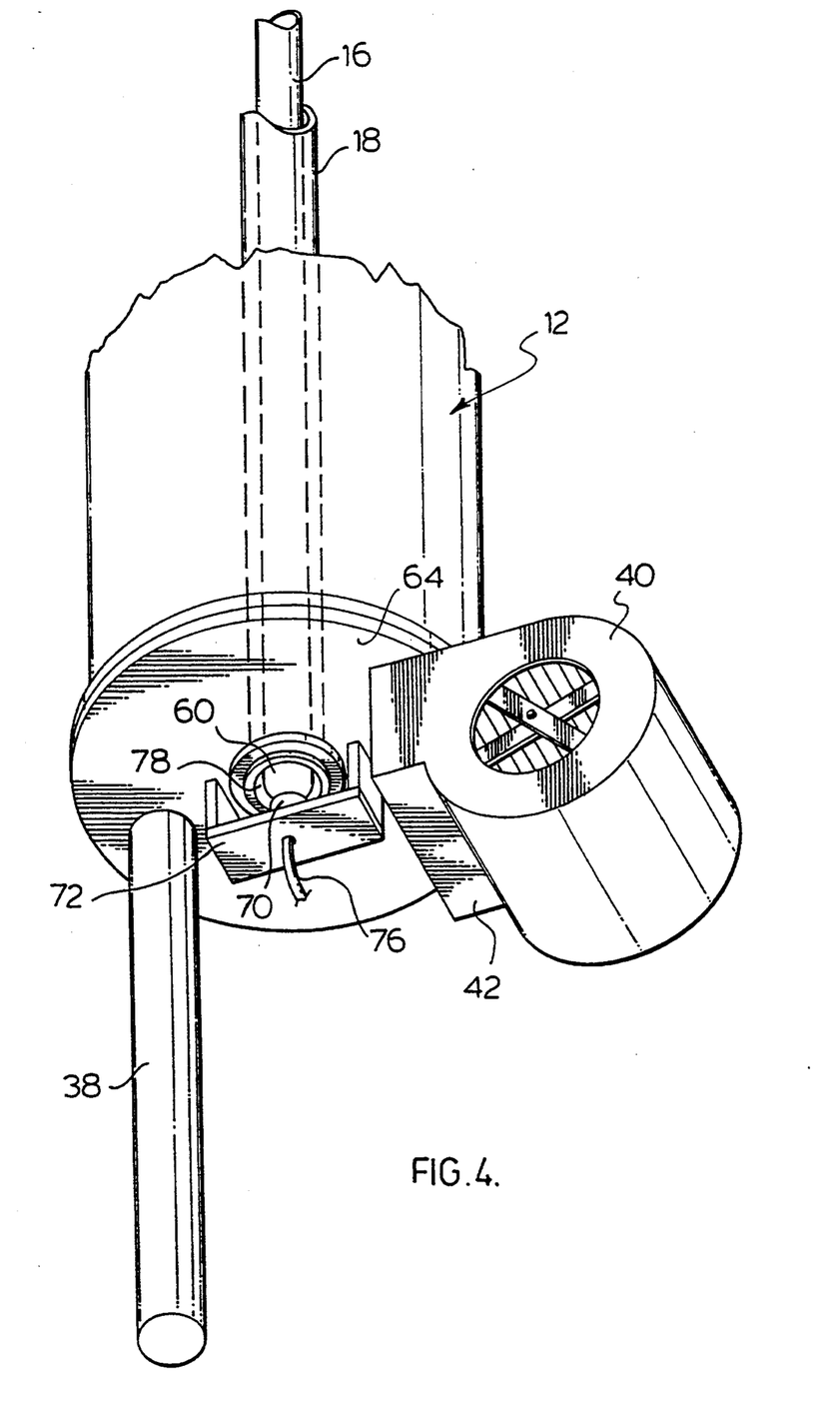
FIG. 4 is a perspective view of the bottom end of the reactor of FIG. 1 showing a preferred arrangement for the cooling of the lower end of the lamp assembly.

With reference to FIG. 4, an alternative embodiment for the cooling fan 40 is shown. The duct 42 which directs cooling air onto the lower end 60 of the lamp and the lamp terminal 70 is mounted directly to the and plate 64 of the reactor vessel 12. This minimized the length of the duct 42 and positions a blower 40 much closer to the lamp lower end 60 for directing cooling air onto the lamp end to again protect the heat sensitive portion in the lamp end. Cooling air as directed at the lamp end 60 not only transverses the lamp end but as well some of the cooling air enters the annular opening 78 between the lamp 16 and protective sheath 18. By virtue of the chimney to be discussed in more detail with respect to FIG. 5, a controlled amount of cooling air enters the annular space 78 to provide cooling of the lamp body while maintaining optimum efficiency for lamp operation and output thereof.

Figure 5:
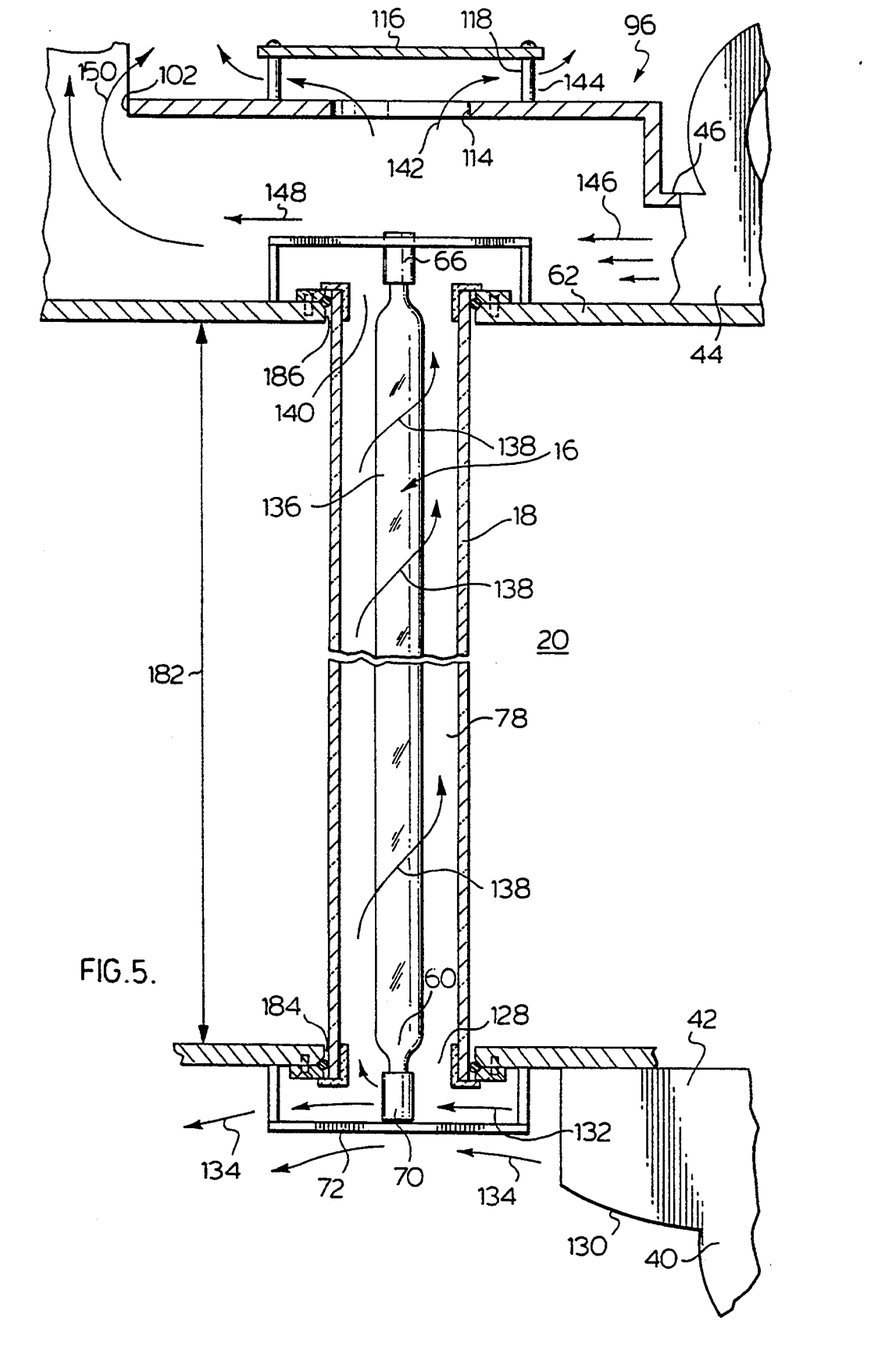
FIG. 5 is a longitudinal section of the lamp assembly of the reactor of FIG. 1 illustrating the flow of cooling air over the lamp ends as well as upwardly over the lamp body portion.

The lamp is supported within the protective sheath 18 by bottom support 72. The bottom support 72 is of a geometrical shape which leaves the lower open end 128 for the protective sheath 18. This allows cooling air to flow freely over the lower lamp end 60 as well as the lamp tip 70. The duct 42 has an upwardly directed baffle portion 130 which directs some of the air flow upwardly in the direction of arrow 132 while the remainder of the air flows transversely across the lamp end in a direction of arrows 134. Hence, the majority of the air that flows transversely across and cools the lamp end 60 and the tip 70 is vented from the base cabinet 36 through a suitable vent 136 as shown in FIG. 2. During start-up of the lamp 16 the lamp body 136 which is constituted by the long cylindrical portion begins to heat up. During the heating process due to electrical discharge between the lamp ends 66 and 70, mercury vapour within the lamp is vaporized until a medium pressure of approximately 8 atmospheres is built up within the lamp. As the lamp body 136 is heated, air within the annular space 78 is also heated by conduction so that air commences to rise within the annular portion 78 in the direction of arrows 138. The open upper end 140 of the protective sheath 18 allows the rising air to flow freely over the lamp end 66. If the fan 44 is not operating, the air flows upwardly in the direction of arrows 142 and is exhausted through the opening 114 beneath plate 116 and through the space 144 as provided by the posts 118. Normally however blower 44 is operating while the lamp 16 is operating, although in a cool ambient environment the fan start may be delayed until ignition of the mercury has started. Blower 44 through duct 44 directs air in the direction of arrows 146 transversely of the lamp tip 66 to cool the lap so that the cooling air, after having passed the lamp end 66 moves through the remainder of the enclosure in the direction of arrow 148. In this arrangement the air is vented in a direction of arrows 150 through the opening 102 of the enclosure 96.

As already mentioned, it is important to control the amount of cooling air flowing over the lamp body 136. By overcooling the lamp body 136 optimum operation of the lamp is not achieved and can result in extinguishing the lamp operation or failure to start the lamp. Hence, it is important to control the amount of air flowing transversely over the lamp ends as well as the amount of air flowing upwardly of the annular space 78. In accordance with the embodiment of FIG. 5 control of cooling air flowing over the lamp body 136 is achieved by controlling the respective outputs of cooling blowers or fans 40 and 44. By virtue of the chimney effect within space 78 the upward flow of air in that space withdraws a portion of the air flowing transversely of the lower end 60 of the lamp into the space 78. This will continue as long as the pressure created by the air flowing transversely of the upper tip 66 is lower than the pressure at the open end 128 of the sheath.

As a starting point in establishing the pressure differential, sufficient air is delivered through duct 46 transversely of the upper end 66 to effect sufficient cooling thereof so that normal operation of the lamp overheating of the temperature sensitive terminal portion is not achieved. Fan 40 is then operated at a speed which develops a slightly greater pressure at open end 128 compared to the pressure at open end 140 so that air continues to flow upwardly of the annular space 78 and thereby withdraws a portion of the air, as indicated by arrow 132 from the fan duct 42, to enhance cooling of the lamp body 136. The capacity of the fan 40 and the configuration of the duct 42 is such that overcooling of the lamp body 136 is avoided because the pressure developed at the open lower end 128 is higher than the pressure developed at open end 140. This ensures that sufficient air flows over the body portion 136 to effect cooling of the lamp body without overcooling the lamp body and extinguishing its operation or reducing the lamp efficiencies.

An additional factor which is considered in the cooling of the lamp body 136 is the cooling of fluids flowing through the reactor chamber 20 and over the sheath 18. It is understood that many fluids which pass through the annular chamber 20 of the reactor will effect a cooling of the sheath 18 which is heated by the operating lamp body 136. Hence, by convection further cooling of the lamp body can be achieved when fluids being treated are at a temperature normally in the range of 20° to 30° C. Considering that the lamp operates at very high temperatures this is a significant temperature gradient. Hence, a reasonably significant cooling factor is achieved by fluids flowing over the protective sheath 18.

In accordance with the embodiment of FIG. 5 system components are provided to direct transversely of each lamp end cooling air wherein a controlled manner the pressure at the lower end exceed the pressure at the upper end. Then, by virtue of the chimney effect within the protective sheath between the lamp and the sheath, air drawn from the lower transversely flowing portion, flows upwardly of the sheath. The fan at the bottom may be further modified by having a baffle which directs the air upwardly of the sheath. By this effect of control in the amount of air flowing upwardly through the sheath proper cooling of the lamp body is achieved to ensure that it remains at its optimum operating temperature.

Figure 6:
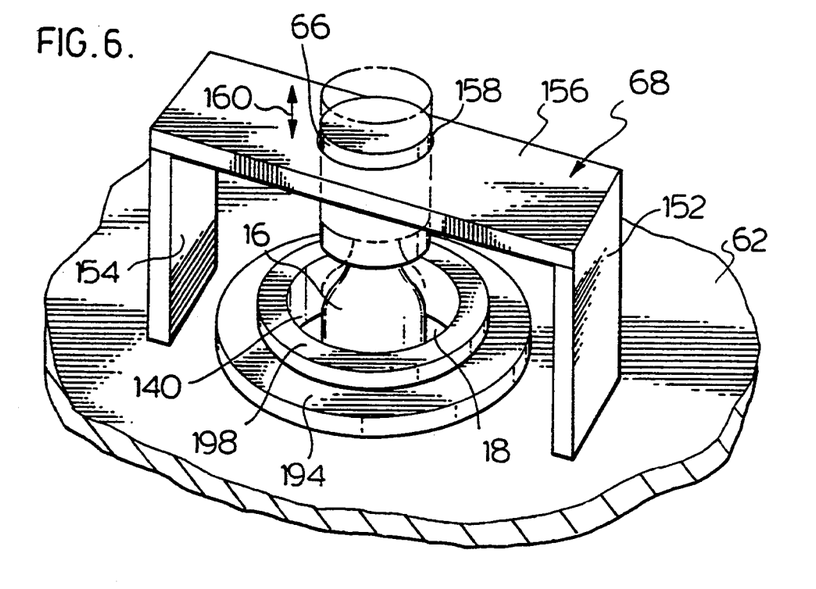
FIG. 6 is a perspective view of the upper lamp end support assembly which accommodates longitudinal expansion and contraction of the lamp.
Figure 7:
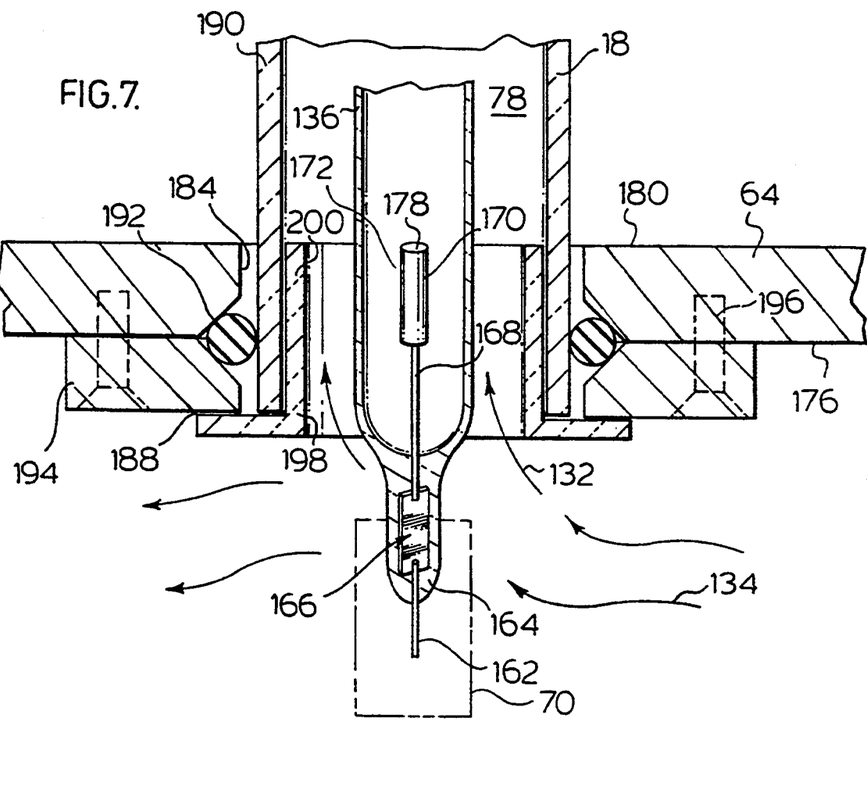
FIG. 7 is a section through the lower portion of the lamp assembly.

Other considerations with respect to lamp cooling and operation are shown in FIGS. 6 and 7. In FIG. 6 further details of the lamp support 68 are shown. The lamp support 68 is geometrically configured to allow unrestricted flow of air upwardly out of the upper end 140 of the annular space between the sheath 18 and the lamp 16. The support 68 consists of two upstanding members 152 and 154 which supports the cross-member 156. The cross-member 156 includes an aperture 158 which in size is greater than the upper lamp end 66. This allows the lamp end 66 to move freely up and down relative to the aperture 158 in a direction of arrow 160. As shown in FIG. 5 the bottom support 72 is fixed with the lamp lower end 70 attached for seated thereon. As the lamp body 136 begins to heat up due to start-up of the lamp the quartz material of the lamp body expands so that the lamp extends longitudinally. As indicated by arrow 160 the lamp end 66 is free to move upwardly of the lamp support 156. This avoids any damage or warping in the lamp body during high temperature operation.

In FIG. 7 further details of the lower portion of the reactor as well as the lamp end are shown. It is appreciated that the details of the lower lamp end are similarly provided at the upper lamp end 66. Furthermore, for purposes of illustration, the lamp is drawn in a distended manner to better illustrate the end components. In an actual lamp, the end portion is considerably more compact. In the lower lamp end 70 a ceramic tip is provided through which an electrical lead 162 extends outwardly of the ceramic end. The lead 162 enters the quartz tip 164 and is connected to a metal ribbon 166. Also attached to the metal ribbon 166 is electrical lead 168 which is connected to the lamp electrode 170. The electrode 170 is housed within the lamp body 136. In order to seal the lamp body space 172, the quartz in the region of metal ribbon 166 is compressed about the ribbon to effect a seal on the flat planar region 174. This prevents escape of gas from the open region 172 along electrical lead 168 particularly when the lamp operating at medium pressures in the range of 8 atmospheres. As already mentioned a similar structural arrangement exists at the upper end 66 of the lamp.

The cooling air which flows transversely of the lower lamp end in the direction of arrow 134 cools the temperature sensitive metal ribbon 166. The metal ribbon 166 deteriorates when the temperature of the lamp end exceeds approximately 350° C. This prevents the lamp body from overheating due to whatever malfunction and hence, prevent melt down of the lamp within the reactor with consequence significant damage to the reactor. It has been found that in the use of such high intensity, high temperature lamps in the reactor, if the lamp end is not properly cooled the lamp end will exceed temperatures of 350° C. Therefore to protect the lamp, the type of cooling as discussed with FIG. 5 and is shown in more detail in FIG. 7, is required to protect the temperature sensitive portion 166 of each lamp end. Also as shown in FIG. 7, in order to provide the necessary cooling air within the space 78 of the protective sheath, air flows upwardly in the direction of arrow 132.

The positioning of the temperature sensitive portion of the lamp end is therefore exterior of the outside portion 176 of the lower end cap 64 for the reactor. Similarly, the upper end 66 of the lamp as shown in FIG. 6 is above the upper end cap 62. In this manner the transversely directed cooling air, as shown in FIG. 5 passes over the temperature sensitive portions of the lamp without directly impinging upon the electrodes 170 as positioned within the protective sheath 18 at the lower and upper ends of the reactor.

In terms of design it is preferred that the end of the electrode 178 is positioned close to the level 180 of the interior of end plate 64. Surface 180 of end plate 64 and the corresponding surface of end plate 62 indicates the reactor length as shown by arrow 182 in FIG. 5. This reactor length is preferably equal to or greater than the distance between electrode ends 178 of the electrodes 170 at each end of the lamp. This distance is commonly referred to as the arc length of the lamp. It is only in the region between the electrodes 170, that UV radiation is emitted. This reduces the amount of radiation which is emitted in a direction outwardly from the protective sheath and either downwardly into the enclosure 36 or upwardly into the enclosure 96. Furthermore, this minimizes the amount of radiation that impinges on components exterior of the protective sheath 18. This is important particularly with respect to components in the system that are sensitive to UV radiation.

Also as shown in FIG. 7, each end of the protective sheath 18 is sealed to the end cap 64 within the opening 184 for the lower end cap and 186 for the upper end cap as shown respectively in FIGS. 5 and 7. At each end cap a compressible O-ring seal 188 is provided. The O-ring is wedged between the outer surface 190 of the protective sheath and the slanted seat portion 192 of the end cap. In order to compress the O-ring 188 within the space between the seat 192 and the surface 190 an annular clamp 194 is provided which is bolted to the end caps by bolts 196 to effect a seal between the opening 184 and the surface 190 of the protective sheath. In this manner, liquid is normally precluded from dripping downwardly from the reactor end cap and interfering with any components albeit electrical or mechanical beneath the reactor base.

Normally the compressible O-ring seal 188 is made of material which is sensitive to excessive heat and UV deterioration. When this is the case a suitable protective collar 198 is provided which prevents radiation emitted at the end of electrode 178 impinging on the heat and UV radiation sensitive O-ring 188. In view of the high temperature of operation of the lamp the collar 198 is formed of a ceramic material which blocks the heat and UV radiation which would otherwise be transmitted through the protective sheath 18 and as well protects the O-ring from heat emitted by the lamp since the ceramic is able to withstand the high temperatures of the lamp as well as act as an insulator for the O-ring material. Similarly, a collar 198 is positioned and secured in the upper end cap 62. The collar 198 must not touch the quartz adjacent to the O-ring or thermal conduction will eventually destroy the O-ring.

Figure 8:
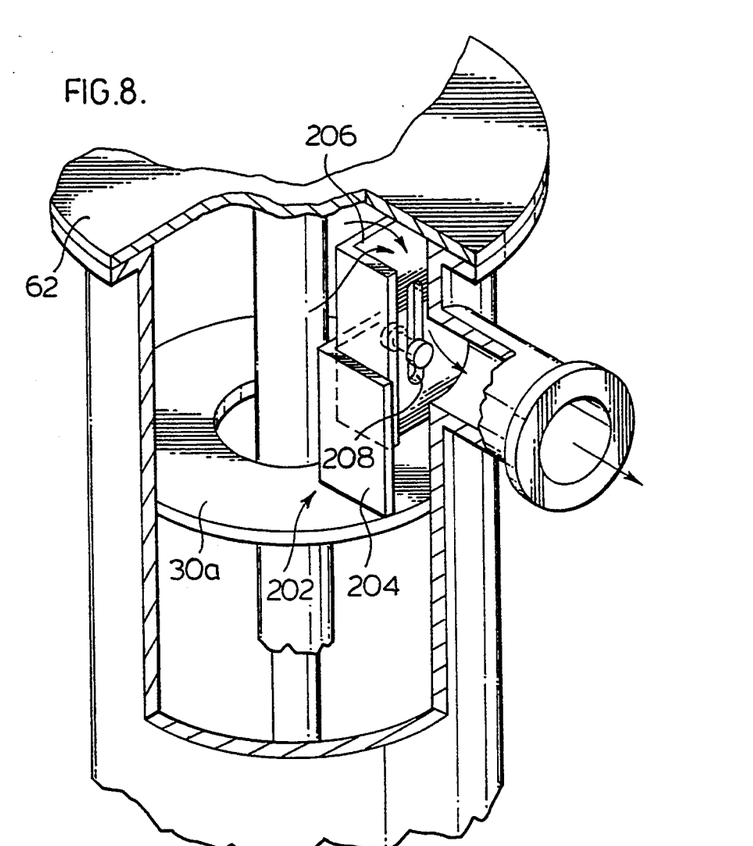
FIG. 8 is a cutaway view of the upper portion of the annular reactor interior showing a flow control device.
Figure 9:
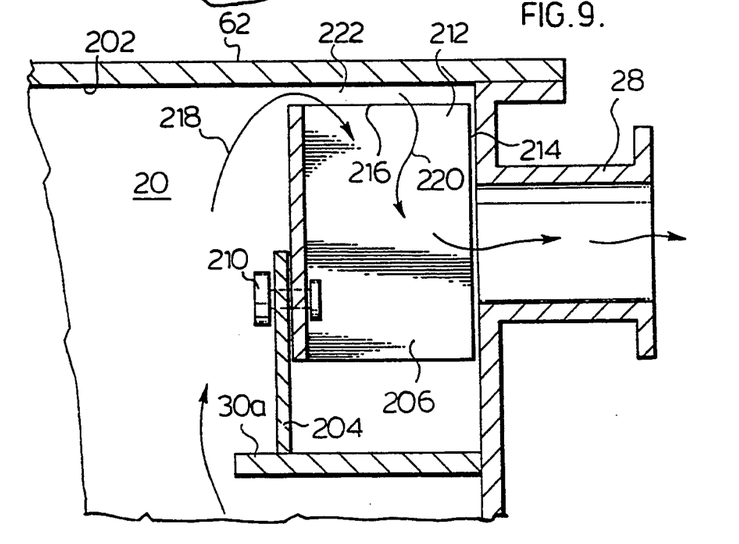
FIG. 9 is a section through the flow control device of FIG. 8.

During operation of the reactor system with fluids flowing therethrough, particularly liquids which contain air bubbles, it is possible to develop an air pocket in the upper region of the reactor. This is undesirable because any air pocket beneath the upper end cap 62 can reduce the amount of cooling applied to the sheath 18 and hence, cooling of the upper end of the lamp within the reactor length 182. It is therefore important to minimize the formation of any air pockets in the upper region of the reactor and in particular, above the uppermost baffle within the reactor. As shown in FIG. 8 above the uppermost baffle 30a, an air pocket eliminator device generally designated 202 is provided. The purpose of the device is to ensure that liquid extends all the way up to the underside 204 of the upper end cap 62 of the reactor as shown in FIG. 9. The air pocket eliminator consists of a bracket 204 which is secured to the uppermost baffle 30a. Bracket 204 supports a movable weir 206. As shown in FIG. 8 movable weir 206 has a slot 208 provided therein through which adjustable bolt 210 is provided. This allows positioning of the weir 206 at the desired height within the annular reactor chamber 20. Once the desired position for the weir 206 is determined the bolt 210 is welded in its clamped position to maintain the weir at the desired height. The weir is U-shaped in cross-section. Each leg 212 abuts the interior 214 of the reactor. The only way liquid can exit the reactor through the outlet 28 is to flow upwardly over the upper edge 216 of the weir in the direction of arrows 218 and 220. The space 222 between the upper edge 216 of the weir and the underside 202 of the end cap is determined by adjusting the height of the weir 206 such that the flow rate of liquids through the reactor is such that liquid fills the entire underside of the end cap 62. This avoids having to locate the outlet 28 in the end cap 62. The laterally directed outlet ensures a transverse flow of liquid across the upper underside of the end cap 202 thereby removing any air which may collect at the other end of the reactor located diagonally opposite the outlet 28.

Accordingly, the reactor system provides a system which readily accommodates the use of the high temperature UV lamps in an economical effective manner. The design also allows for varying the reactor diameter by selecting the appropriate size for the protective sheath 18 and the outer diameter of the reactor shell 14. In this manner the distance provided through the reactor compartment for a particular reaction may be determined based on the absorption of the UV radiation within the liquids being treated. By provision of the balanced cooling air for the lamp in the manner suggested with respect to FIG. 2 optimum output of the lamp is achieved by use of suitable controllers. The lamp output during its life may be varied to always provide for the desired output of radiation during treatment of liquids flowing through the system. It is also appreciated that the quality of the quartz for the lamp and the protective sheath is such that radiation emitted by the lamp is transmitted through to the fluids. Preferably the protective sheath has a wall thickness of less than 3 mm and preferably in the range of 2 mm. Normally, all gaskets used in sealing the reactor end caps and the like are of a Viton TM material which is UV resistant and as well as ozone resistant. It may also be desirable to provide at the base of the reactor a drip rail to collect condensation which may flow down the outside of the reactor particularly when the reactor is operating in humid environment and a cool fluid is being treated.

As already discussed, several interlocks may be provided in controlling the reactor operation. This is important from the standpoint of ensuring that the reactor is shut down at any time when a particular fault is detected. Such fault detections include voltage to the lamp being outside of a selected range, lamp exceeding predetermined temperatures as detected by suitable temperature sensors at the lamp upper and lower ends, sensing of openings of various access covers including the lid 120 for the enclosure 96 or the door 37 in the enclosure base 36. Operation of the cooling fans 40 and 44 is sensed and in the event of failure of either fan, operation of the lamp is ceased.

By virtue of the individuality of the reactor design it is also possible to provide several reactors in a series so that in each reactor a particular phase of decontamination can be carried out. In this manner a variable multi-stage treatment can be provided where the decontamination process carried out in the first reactor can be different from the decontamination process carried out in the next serially connected reactor.

Although preferred embodiments of the invention are described herein in detail, it will be understood by those skilled in the art that variations may be made thereto without departing from the spirit of the invention or the scope of the appended claims.

We claim:

1. A reactor assembly for destroying contaminants in fluids solely by the application of UV radiation to promote such destruction, said reactor assembly comprising:
   i) a vertically oriented cylindrical reactor column with an inlet at one end to introduce fluids to said reactor and an outlet at another end to remove treated fluids from said reactor,
   ii) a vertically oriented UV radiation emitting lamp operating at temperatures in excess of 300° C. and positioned centrally of said reactor column,
   iii) a cylindrical protective sheath transparent to UV radiation for said lamp, said sheath being concentric with said lamp and isolating said lamp from an interior surface of said reactor column, said reactor column in combination with said sheath defining an annular reactor space through which fluids to be treated flow from said reactor inlet through to said reactor outlet, whereby fluid flow along said sheath effects cooling of said sheath due to lamp heating,
   iv) an end cap for each end of said reactor column, said end caps having aligned centrally located openings to receive corresponding ends of said sheath, whereby each end of said sheath opens outwardly of said end cap,
   v) means for operatively circumferentially sealing respective end portions of said sheath to said end cap openings to retain thereby fluids being treated in said annular reactor space,
   vi) said lamp having an upper terminal and a lower terminal, each terminal having a corresponding temperature-responsive portion formed to break electrical connection with electrodes within the lamp when heated to a predetermined temperature exceeding 350° C., said lamp being of a sufficient length to extend said terminals and position said temperature sensitive portions beyond corresponding open ends of said sheath, said lamp having an arc length and said reactor having a reactor length defined by said end caps, said reactor length being equal to or greater than said arc length,
   vii) means for supporting each said terminal at a corresponding reactor end, each of said support means having a lamp engaging portion which transverses said open ended sheath in a manner which provides air communication with sheath interior,
   viii) means for directing cooling air onto each of said upper and lower terminals to cool said temperature sensitive portions thereof and thereby prevent deterioration of said lamp terminals due to excessive heating, said sheath having an internal diameter greater than an external diameter for said lamp, said means for directing cooling air onto said lower terminal being adapted to develop an air pressure value at a lower end of said sheath greater than an air pressure value at an upper end of said sheath, whereby a controlled constant flow of cooling air is assured upwardly of said sheath and over said lamp by virtue of said sheath lower and upper ends being open outwardly of said lower and upper end caps, such constant flow of cooling air being controlled to permit said lamp to operate at optimum operating temperatures.

2. A reactor assembly of claim 1 wherein said means for directing cooling air onto said upper terminal end comprises means for enclosing said open upper end of said sheath to preclude direct eye exposure to UV radiation, said enclosing means defining a plenum above said upper reactor end cap, said enclosing means being a vent provided therein to exhaust cooling air therefrom, said means for directing cooling air into said plenum developing a backpressure of air in said plenum, said means for directing cooling air onto said lower terminal end developing a pressure at said lower end of said sheath which exceeds air backpressure in said plenum during operation of said reactor assembly.

3. A reactor assembly of claim 2 wherein said reactor column is supported on a cabinet with at least said lower lamp terminal housed in said cabinet to preclude direct eye contact exposure to UV radiation.

4. A reactor assembly of claim 1 wherein said lamp operates at temperatures in the range of 700° C. to 1100° C.

5. A reactor assembly of claim 1 further comprising:
   ix) means for directing flow of fluids along said annular space in an inward and outward manner to vary thereby radial spacing of any portion of fluids flowing along said reactor relative to said centrally located lamp.

6. A reactor assembly of claim 5 wherein said means for directing flow of fluids comprises a plurality of baffles spaced along said annular reactor space.

7. A reactor assembly of claim 6 wherein said baffles comprise a plurality of spaced apart concentric rings, each of said rings having an outer circumference which engages an inner circular surface of said reactor and an inner circumference which is spaced from said sheath, said baffles directing fluids to flow inwardly and outwardly relative to said lamp and promoting increased fluid velocities adjacent said sheath.

8. A reactor assembly of claim 7 wherein said spacing between said sheath and said inner circumference of each ring is predetermined in accordance with a range of fluid flowrates through said reactor to induce mixing in the flow of fluid adjacent said sheath as the fluid flows between said respective ring and said sheath.

9. A reactor assembly of claim 8 wherein said spacing between said sheath and said inner ring circumference accommodates periodic travel of a sheath cleaning device along said sheath.

10. A reactor assembly of claim 8 wherein said predetermined spacing is minimized to induce turbulence in the flow of fluid adjacent said sheath and in the region of each baffle.

11. A reactor assembly of claim 8 wherein each of said baffles extends into said annular reactor space by at least 25% of the radial dimension of said annular reactor space.

12. A reactor assembly of claim 7, wherein said baffle uppermost of said reactor and adjacent said outlet prevents backmixing of fluids above said uppermost baffle with fluids beneath said uppermost baffle by virtue of said positive flow of fluids upwardly between said uppermost baffle and said sheath.

13. A reactor assembly of claim 1, wherein uppermost of said reactor column is provided means for preventing formation of an air pocket adjacent said upper end cap, said means for preventing formation of an air pocket comprising a catch basin at said outlet and in communication with said outlet, said catch basin having an opening uppermost of said reactor column and of a cross-sectional size to restrict flow of treated fluids into said catch basin and through said outlet, said catch basin opening restricting a flow rate of treated fluid to fill thereby said reaction column and prevent thereby formation of an air pocket uppermost of said reactor column.

14. A reactor assembly of claim 1 wherein said means for supporting each said lamp terminal, includes means for allowing said lamp to extend and contract longitudinally due to lamp heating and cooling during use.

15. A reactor assembly of claim 14 wherein said support means at the lower end cap of said reactor fixes said terminal, said support means at the upper end cap of said reactor comprises an aperture through which said lamp terminal extends and is free to move to allow thereby lamp extension and contraction.

16. A reactor assembly of claim 14 wherein each of said support means is of a geometrical shape to position each terminal end at least 7.5 cm away from ground potential.

17. A reactor assembly of claim 14 wherein each of said support means has a U-shaped portion where said U-shaped portion transverses said open ended sheath with the legs of said U-shaped portion secured to said respective end cap.

18. A reactor assembly of claim 17 wherein said support means is formed of a ceramic material.

19. A reactor assembly of claim 1 wherein said means for sealing each said end portion of said sheath to said reactor cap comprises an O-ring seal interposed said end cap opening and said sheath and means for holding said O-ring in a sealing position.

20. A reactor assembly of claim 19 wherein a temperature and UV resistant collar is provided at each sheath end to block UV radiation and heat emitted by said lamp, impinging on said corresponding O-ring.

21. A reactor assembly of claim 20 wherein said collar is ceramic.

22. A reactor assembly of claim 21 wherein said collar is spaced from said sheath and said lamp.

23. A reactor assembly of claim 1 wherein said sheath is formed of of quartz, said quartz sheath having a wall thickness of less than 3 mm.

24. A method for decontaminating a fluid solely by application of UV radiation to said fluid, said UV radiation being produced by a lamp operating at temperatures in excess of 300° C., said method comprising:
  i) passing said fluid to be treated through a vertically oriented cylindrical reactor chamber having an exterior shell, with said UV lamp extending along said chamber and located centrally thereof, said lamp being isolated from said reactor chamber by an enclosing cylindrical sheath which is transparent to said UV radiation, said sheath being larger than said lamp to provide an annular space between said lamp and sheath, said reactor chamber having a reactor length which is equal to or greater than an arc length for said lamp,
  ii) positioning each lamp terminal exterior of respective ends of said sheath with temperature sensitive portions of each terminal exposed beyond said sheath ends, said temperature sensitive portions being formed to break electrical connection with electrodes within the lamp when heated to a predetermined temperature exceeding 350° C.,
  iii) passing cooling air over respective terminals of said lamp to cool said temperature sensitive portions thereof and thereby prevent deterioration of each lamp end due to excess heating during lamp operation,
  iv) developing sufficient air pressure at the lower end of said sheath which exceeds air pressure at the upper end of said sheath to ensure a constant upward flow of air along said annular space within said sheath to provide thereby additional cooling for and prevent overheating of said lamp during operation at temperatures in excess of 300° C.

25. A method claim 24 wherein said reactor chamber is annular in cross section, annular ring baffles being positioned in said cylindrical reactor chamber along its length, said baffles being spaced apart along said reactor chamber length, each baffle ring contacting said reactor chamber exterior shell and having an inner portion spaced from said sheath to define thereby a plurality of serially arranged annular reactor compartments,
  said method comprising passing said fluids upwardly through said reactor chamber whereby said baffles direct flows of fluids inwardly and outwardly relative to said sheath as fluids flow from one annular reactor compartment to another annular reactor compartment.

26. A method of claim 24 comprising the further steps of detecting an interruption of cooling air flow over at least one of said upper and lower lamp terminals and,
  upon detection of such interruption of air flow, de-energizing said lamp to prevent damage thereto.

27. A method of claim 24 comprising the further step of detecting an interruption of fluid flow through said reactor chamber, and
  upon detecting such interruption of fluid flow, de-energizing said lamp to prevent lamp damage.

28. A method of claim 24 comprising the further step of selecting a reactor chamber outer diameter which defines a desired radial UV radiation pathlength through the annular portion of said chamber, said desired pathlength being determined by an extent of UV radiation absorbence of said fluid flowing through said reactor.

29. A multi-stage system for treating contaminated fluids in multiple stages comprising a multiple arrangement according to at least two reactor assemblies of claim 1, said reactor assemblies being arranged in a serial manner with the outlet of a first reactor assembly connected to the inlet of a second reactor assembly whereby fluids treated in accordance with first processing parameters in said first reactor assembly are treated in said second reactor assembly in accordance with second processing parameters.

* * * * *